United States Patent [19]

Powell

[11] Patent Number: 5,252,337
[45] Date of Patent: Oct. 12, 1993

[54] CONTROLLED RELEASE CALCIUM CHANNEL BLOCKER MICROCAPSULES

[75] Inventor: Thomas C. Powell, West Alexandria, Ohio

[73] Assignee: Eurand America, Inc., Ohio

[21] Appl. No.: 720,978

[22] Filed: Jun. 25, 1991

[51] Int. Cl.$^5$ .................. A61K 9/62; A61K 9/64; B01J 13/06

[52] U.S. Cl. .................. 424/456; 424/452; 424/461; 424/480; 424/492; 424/495; 427/213.31; 427/213.32; 427/213.33; 427/213.36; 428/402.24; 514/821; 514/963; 514/965

[58] Field of Search .......... 427/213.31, 213.32, 427/213.33, 213.36; 428/402.24; 424/452, 456, 461, 480, 492, 495; 514/821, 963, 965

[56] References Cited

U.S. PATENT DOCUMENTS

| | | | |
|---|---|---|---|
| 3,155,590 | 11/1964 | Miller et al. | 424/495 |
| 3,341,416 | 9/1967 | Anderson et al. | 424/495 |
| 3,835,221 | 9/1974 | Fulberth et al. | 424/458 |
| 4,259,315 | 3/1981 | Lippmann et al. | 424/459 |
| 4,308,251 | 12/1981 | Dunn et al. | 424/480 X |
| 4,411,933 | 10/1983 | Samejima et al. | 427/213.3 |
| 4,443,497 | 4/1984 | Samejima et al. | 427/213.36 |
| 4,462,982 | 7/1984 | Samejima et al. | 424/495 |
| 4,542,042 | 9/1985 | Samejima et al. | 427/213.36 |
| 4,574,080 | 3/1986 | Roswall et al. | 424/458 |
| 4,606,940 | 8/1986 | Frank et al. | 427/213.32 |
| 4,689,233 | 8/1987 | Dvorsky et al. | 424/456 X |
| 4,721,619 | 1/1988 | Panoz et al. | 424/459 |
| 4,832,958 | 5/1989 | Baudier et al. | 424/473 |
| 4,853,249 | 8/1989 | Takashima et al. | 424/468 X |
| 4,886,668 | 12/1989 | Haslam et al. | 424/457 X |
| 4,888,177 | 12/1989 | Gergely et al. | 424/466 |
| 4,891,230 | 1/1990 | Geoghegan et al. | 424/461 |
| 4,894,240 | 1/1990 | Geoghegan et al. | 424/490 X |
| 4,895,726 | 1/1990 | Curtet et al. | 424/452 X |
| 4,917,893 | 4/1990 | Okada et al. | 424/423 |
| 4,917,899 | 4/1990 | Geoghegan et al. | 424/461 |
| 4,925,672 | 5/1990 | Gremm et al. | 424/489 X |
| 4,938,967 | 7/1990 | Newton et al. | 424/458 |
| 4,954,298 | 9/1990 | Yamamoto et al. | 264/4.6 |
| 4,960,596 | 10/1990 | Debregeas et al. | 424/458 |
| 4,963,365 | 10/1990 | Samejima et al. | 424/46 |
| 4,971,805 | 11/1990 | Kitanishi et al. | 424/494 |
| 5,000,962 | 3/1991 | Sangekar et al. | 424/482 |
| 5,008,117 | 4/1991 | Calanchi et al. | 424/494 |

OTHER PUBLICATIONS

Kirk-Othmer, Encyclopedia of Chemical Technology, p. 485, 1981.

*Primary Examiner*—Richard D. Lovering
*Attorney, Agent, or Firm*—Steven H. Flynn

[57] ABSTRACT

A controlled release formulation of a calcium channel blocker for oral administration contains non-pareil seeds loaded with a calcium channel blocker, particularly diltiazem, nifedipine, or verapamil, and then microencapsulated in ethylcellulose by phase separation techniques. The resultant microcapsules provide an approximately zero order release rate, preferably over 12 to 16 hours. These microcapsules may be filled into gelatin capsules.

18 Claims, 2 Drawing Sheets

CONTROLLED RELEASE CALCIUM CHANNEL BLOCKER MICROCAPSULES

BACKGROUND OF THE INVENTION

This invention pertains to a sustained release formulation of calcium channel blockers microencapsulated by ethylcellulose and the process for preparing the formulation. Calcium channel blockers, such as diltiazem, nifedipine, and verapamil, modulate the transmembrane influx of calcium ions into both smooth and cardiac muscle. As the contractile processes of these muscles are dependent upon the movement of extracellular calcium ions into their cells, use of calcium channel blockers results in potent cardio-vascular effects. These results include decreased vascular resistance, slowed atrioventricular (A-V) conduction, reduced contractile tension, and reduced oxygen requirement of the heart muscle. Furthermore, the reduced calcium influx produced by calcium channel blockers interferes with excitation-contraction coupling of vascular smooth muscle, offering the therapeutic advantage of concomitant coronary and systemic vasodilation similar to the effect exerted by nitrates. Calcium channel blockers have been shown to be useful in alleviating symptoms of chronic heart disease, particularly cardiac arrythmias and essential hypertension.

Calcium channel blockers are conventionally administered in tablet or capsule form. Recently, a patent for a sustained release tablet formulation of diltiazem has issued in which release rate is controlled by the application of a diffusion controlled membrane to a matrix tablet containing swellable hydrophilic polymers (U.S. Pat. No. 5,000,962, Sangekar, et al.).

Other formulations of calcium channel blockers have also been patented. Ecanow suggests incorporation of veramapil hydrochloride into a coacervate-based, matrix-enveloped composition (U.S. Pat. No. 4,963,367). Microcapsules of diltiazem are also suggested for injectable preparations. Okada, et al. prepare these microcapsules in a water-in-oil emulsion (U.S. Pat. No. 4,917,893 and Yamamoto, et al. prepare these microcapsules in a water-in-oil-in-water emulsion (U.S. Pat. No. 4,954,298). More recently, Debregeas, et al. disclose a slow release Galenical preparation of diltiazem (U.S. Pat. No. 4,960,596).

Gergely, et al. disclose instant granules which contain a granulated carbohydrate carrier material, and a coating which is insoluble in water containing the pharmaceutically active ingredient (U.S. Pat. No. 4,888,177). Kitanishi, et al. disclose slow releasing granules characterized by coating quick-releasing granules which contain the active ingredient, polyvinylpyrrolidone, and a disintegrator (U.S. Pat. No. 4,971,805). Fulberth, et al. disclose a delayed action drug prepared by coating nonpareils with an adhesive solution, applying the drug, and coating with lacquer (U.S. Pat. No. 3,835,221).

Panoz, et al. disclose a controlled absorption diltiazem pellet with a core of diltiazem in association with an organic acid and a lubricant and a multi-layer outer membrane containing layers of water insoluble and water soluble synthetic polymers. The number of layers and the ratio of polymers are defined so as to result in a specified rate of dissolution (U.S. Pat. No. 4,721,619). Geoghegan, et al. disclose improvements to this general formulation in which the specified rate of dissolution differs from the previous invention (U.S. Pat. Nos. 4,891,230 an 4,917,899).

Microencapsulation technology ha long been used for the controlled delivery of pharmaceuticals. As early as 1964 aspirin was encapsulated in ethylcellulose (Miller, et al., U.S. Pat. No. 3,155,590) with improvements made to the basic process by Anderson, et al. (U.S. Pat. No. 3,341,416). Microencapsulation has also been used to deliver potassium salts to humans (Lippmann, et al., U.S. Pat. No. 4,259,315).

Other drugs have also been microencapsulated using variety of methods. For example, Newton, et al. disclose microcapsules with a higher than usual density by including a weighting agent, such as barium sulphate, to increase the residence time in the stomach (U.S. Pat. No. 4,938,967). Roswell, et al. disclose a controlled release formulation which contains additional particles of the active substance adhered to the surface of the coating (U.S. Pat. No. 4,574,080). Frank, et al. disclose a process for encapsulation by dissolving the compound to be encapsulated in a solvent, mixing the solution with a solution of encapsulating material and electrolyte, and gelling the encapsulating material (U.S. Pat. No. 4,606,940).

Microencapsulation technology has also been used for the controlled delivery of calcium channel blockers. The following are some examples.

Samejima, et al. disclose various microcapsules and processes of producing the same. Microcapsules of ethylcellulose are disclosed by flocculation in the presence of an organosilicon polymer and optionally a surfactant (U.S. Pat. No. 4,411,933); by incorporation of a polymer material which shows at least a 1.2 times increase in weight by immersion in water at 37 degrees C. (U.S. Pat. No. 4,462,982); and by use of a phase-separation-inducing agent soluble in cyclohexane, having a molecular weight of 150-3,000 and a solubility parameter of 7-10 cal/cm (U.S. Pat. No. 4,542,042).

Samejima, et al. also disclose free-flowing microcapsules of various coating materials by effecting the phase separation-flocculation of the coating polymer in the presence of ethylcellulose to minimize the coagulation of the coating polymer (U.S. Pat. No. 4,443,497) and a controlled release dosage which contains an inner core of medicament, an inner coating of ethylcellulose and a hydrophobic substance, and an outer coating of medicament (U.S. Pat. No. 4,963,365).

One of the primary reasons for encapsulating a drug is to slow the release of the drug into the body. Thus, a controlled release microencapsulated formula may be substituted for several non-microencapsulated doses. The release rate of the drug is typically controlled primarily through the thickness of the coating. Typically the release pattern is first order in which the rate decreases exponentially with time until the drug is exhausted (Kirk-Othmer, *Encyclopedia of Chemical Technology*, p.485, 1981). This release pattern is due to the fact that the concentration difference between that inside and that outside the capsule decreases continuously during dissolution.

However, often a zero order, constant-release rate is preferred in which case the microcapsules deliver a fixed amount of drug per unit time over the period of their effectiveness. This invention uses a novel combination of parameters to provide a controlled release, approximately zero order microencapsulated formulation of calcium channel blockers.

SUMMARY OF THE INVENTION

An object of the present invention is to provide an ethylcellulose microcapsulated formulation of a calcium channel blocker with a controlled release from about 8 to about 24 hours, more narrowly from about 12 to about 16 hours. Another object of this invention is to provide an ethylcellulose microencapsulated formulation of a calcium channel blocker with an approximately zero order release rate. A further object of this invention is to provide a process for manufacturing these formulations.

Additional objects will become apparent hereinafter and still other objects will be apparent to one skilled in the art.

These and other objects are accomplished according to the present invention which provides controlled release microcapsules of calcium channel blockers, particularly diltiazem, nifedipine, or verapamil. These microcapsules are prepared by the steps of:

1) loading the drug from solution or dispersion onto a core material to form loaded pellets or granules;
2) dispersing ethylcellulose and, optionally, a phase separation-inducing polymer in an organic solvent, the phase separation-inducing polymer having a higher solubility in the organic solvent than that of ethylcellulose;
3) adding the loaded pellets or granules to the dispersion;
4) heating the dispersion with agitation until the polymers are in solution;
5) cooling the solution to solidify the ethylcellulose and achieve microencapsulation;
6) recovering the microcapsules from the dispersion;
7) drying the microcapsules; and
8) filling gelatin capsules with the microcapsules.

DETAILED DESCRIPTION OF THE INVENTION

The controlled release calcium channel blockers of this invention constitute those containing diltiazem, nifedipine, or verapamil in the core and an outer membrane of ethylcellulose formed by phase separation techniques. Pharmaceutically acceptable salts or the hydrochloric acid forms of these calcium channel blockers may also be used.

The calcium channel blocker is first loaded onto nonpareil seeds or granules to form the core. The core may be any pharmaceutically acceptable, non-functional, solid carrier, including a mixture of sucrose and starch, or potassium chloride. The core may also be a crystal of the calcium channel blocker itself. The calcium channel blocker is applied to the core from an aqueous solution or dispersion containing a binder of any water soluble polymer which is insoluble in cyclohexane, including gum arabic, gelatin, or preferably polyvinylpyrrolidone (PVP). Application of this calcium channel blocker solution or dispersion onto the core may be accomplished using standard techniques known in the art, such as by using a Wurster insert or rotor or by top spraying in a fluidized bed coater. This results in loaded pellets or granules comprising about 40 to about 50 percent of the calcium channel blocker, from about 40 to about 50 percent of core, and from about 2 to about 3 percent of the binder. In accordance with a preferred feature of the present invention, an additional coating of from about 0.4 to about 0.6 percent binder by weight of the core may be deposited to seal the loaded pellets or granules. The loaded granules may then be prilled to obtain relatively smooth, spherical pellets. These relatively smooth, spherical pellets result in more uniform microencapsulation. According to the present invention, the prilling step is preferred for use when the core granules used are not initially smooth and spherical, a step often unnecessary when nonpareils are used. The loaded pellets are next screened to obtain the bulk of the pellets within the desired size range. The size of the loaded calcium channel blocker pellets of this invention are from about 12 mesh to about 50 mesh (1.41–0.289 mm), more narrowly from about 12 mesh to about 30 mesh (1.41–0.548 mm), most narrowly from about 14 mesh to about 20 mesh (1.19–0.841 mm). By narrowing the particle size range, the release rate of the capsule goes from first order to the desired approximately zero order of this invention. In addition, larger sized particles have higher active contents and slower release rates than smaller particles. As the release profile tends to deviate from zero order when the concentration within the microcapsule falls below saturation, this condition is reached earlier in the smaller, less active loaded pellets. Thus, it is preferable that the final loaded pellets of this invention are at least 40% active. The term active, as used herein, means the percent of the core material which is composed of the active calcium channel blocker.

The loaded pellets are next coated with ethylcellulose via phase separation from an organic media to achieve the controlled release. From about two to about ten percent by weight of the loaded pellets of ethylcellulose and, optionally, up to about ten percent by weight of the loaded pellets of a phase separation-inducing polymer are dispersed in an organic solvent, the phase separation-inducing polymer having a higher solubility in the organic solvent than that of ethylcellulose. The phase separation-inducing polymer is preferably polyethylene and the organic solvent is preferably cyclohexane, though other suitable phase-separation polymers and organic solvents may be used. The drug loaded pellets are next added to the dispersion in the phase ratio of ethylcellulose to pellets necessary to achieve the desired thickness of coating. Higher phase ratios will yield a thicker coating and thus a slower release rate. The phase ratio used for this invention should be in the range of 1:5 to 1:50, more narrowly from 1:20 to 1:25. This dispersion is slowly heated with agitation until the polymers are in solution, for example at a temperature of 80 degrees C. The rate of heating is not critical as long as sufficient time is allowed for the constituents to go into solution. The temperature is not critical in the invention as long as the temperature remains below the boiling points of the constituents. The dispersion is then slowly cooled to achieve microencapsulation as the ethylcellulose phase deposits upon the particles of core material and solidifies, for example down to a temperature of 35 degrees C.

The resultant microcapsules are recovered from the media and may be washed with the organic solvent to remove traces of the phase-inducing polymer. Minuscule amounts of this polymer may remain trapped within the ethylcellulose coating and on the surface of the microcapsules, preferably less than 10,000 ppm. The microcapsules are then dried using techniques known in the art, for example by vacuum filtration and tray or fluidized bed drying. The microcapsules may next be screened to obtain sizes from about 10 to about 50 mesh (1.68–0.289 mm), more narrowly from about 10 to about 30 mesh (1.68–0.548 mm), most narrowly from about 12 to about 18 mesh (1.41–0.92 mm). These microcapsules finally may be filled into hard or soft gelatin capsules in desired doses, such as 120 or 240 mg of active calcium channel blocker.

Thus the release rate of the microcapsules of this invention are controlled in three ways; by the phase ratio of ethylcellulose to loaded pellets, by use of relatively smooth, spherical loaded pellets, and by use of a limited pellet size range. In this way, microcapsules are produced which may have a release rate from about 8 to about 24 hours, more narrowly from about 12 to about 16 hours and an approximately zero order release rate.

EXAMPLES

USP, as used herein, refers to the United States Pharmacopeia and the National Formulary Reference 1990 USP XXII/NF XXII.

Example 1

Preparation of controlled release microcapsules of verapamil

Verapamil is loaded onto the non-pareil seeds from an aqueous dispersion containing a binder of water soluble polyvinylpyrrolidone (PVP K-90, average molecular weight 360,000 obtained from GAF) by spraying the dispersion onto the seeds in a fluidized bed coater (Wurster). Three kilograms of verapamil are dispersed in six kilograms of water and 150 grams of PVP K-90. This dispersion is then sprayed onto three kilograms of non-pareil seeds in a fluidized bed coater using a top spray configuration. The loaded verapamil pellets are then screened to obtain the bulk of the granulation with the range of 18 to 20 mesh.

The loaded verapamil pellets are next coated with ethylcellulose via phase separation from an organic media to achieve the controlled release. Fifteen hundred grams of cyclohexane (obtained from Ashland Chemical) are added to a three liter beaker equipped with a four inch turbine propeller for agitation and a heating mantle. With sufficient agitation to keep the constituents well dispersed, 30 grams of polyethylene (Epolene C-10 obtained from Eastman-Kodak) and 20 grams of ethylcellulose (Grade 100, N.F. obtained from Dow) are added. Five hundred grams of loaded verapamil pellets are next added to the system. With continued agitation, the batch is heated to 80 degrees C. over a time period of 30–45 minutes. The heat is then removed from the system and controlled cooled to 35 degrees C. over a time period of 45–60 minutes to cause phase separation and achieve microencapsulation. Agitation is stopped when the batch temperature reaches 35 degrees C. The resultant microcapsules are recovered from the media using vacuum filtration and dried. These dried microcapsules may be filled into gelatin capsules in desired doses (120 or 240 mg active verapamil).

Example 2

Preparation of controlled release microcapsules of diltiazem

The procedure of example 1 is used except that diltiazem is substituted for verapamil. Desired doses are 60, 90, or 120 mg active diltiazem.

Example 3

Variation of preparation

The method of example is followed except that an additional 30 grams of polyvinylpyrrolidone is applied to the loaded pellets prior to microencapsulation as a seal coating.

Example 4

Physical data of Diltiazem Microcapsules

Diltiazem microcapsules in 90 mg active capsules, such as those produced in example 2 were analyzed using standard techniques known to the art.

| Appearance | White microcapsules in a colorless, hard gelatin capsule | |
|---|---|---|
| Assay | 88.5 +/− 4.8 mg/capsule | |
| Content Uniformity | 98.3 +/− 5.% of label calim with 3.% RSD | |
| Drug Capsule Content (Variation) | 32.2% | |
| | High content | 94.9 mg |
| | Low content | 79.8 mg |
| | Range | 15.1 mg |

Example 5

Plasma levels of diltiazem after administration

Diltiazem microcapsules in 90 mg active capsules, such as those produced in example 2, were analyzed in a four patient test using standard techniques known to the art.

| Time (hours) | Plasma Level (ng/ml) | | | | | | |
|---|---|---|---|---|---|---|---|
| | 1 | 2 | 3 | 4 | mean | S.D. | C.V. |
| 0.5 | 0.0 | 0.0 | 0.0 | 0.0 | 0.0 | 0.0 | 0 |
| 1.0 | 0.0 | 0.0 | 0.0 | 0.0 | 0.0 | 0.0 | 0 |
| 2.0 | 5.4 | 5.4 | 3.7 | 13.4 | 7.0 | 4.4 | 62 |
| 3.0 | 12.6 | 13.6 | 8.1 | 54.7 | 22.3 | 21.8 | 98 |
| 4.0 | 38.2 | 14.5 | 10.1 | 44.9 | 26.9 | 17.2 | 64 |
| 6.0 | 83.1 | 15.9 | 31.7 | 84.8 | 53.9 | 35.5 | 69 |
| 8.0 | 88.0 | 17.9 | 24.9 | 57.3 | 47.0 | 32.3 | 69 |
| 10.0 | 58.3 | 20.6 | 24.0 | 35.6 | 34.6 | 17.0 | 49 |
| 12.0 | 43.0 | 19.4 | 15.8 | 26.0 | 26.1 | 12.1 | 46 |
| 16.0 | 24.4 | 12.3 | 8.8 | 18.0 | 15.9 | 6.8 | 43 |
| 24.0 | 10.7 | 5.3 | 4.8 | 6.3 | 6.8 | 2.7 | 40 |

S.D. = standard deviation
C.V. = coefficient of variation

Example 6

Average Bioavailability Data of Diltiazem Product

Diltiazem microcapsules in 90 mg active capsules, such as those produced in example 2, were analyzed in a four (4) patient study (see example 5) using standard techniques known to the art.

| Cmax | 56.3 |
|---|---|
| Tmax | 7.5 |
| AUC | 541.2 | where,
Cmax is the maximum blood level concentration of the diltiazem;
Tmax is the time at which the maximum blood level concentration occurs; and
AUC is the "area under the curve" of time versus blood concentration.

Example 7

Release Rate of Diltiazem Product

The release rate of diltiazem microcapsules was analyzed using USP basket method. These microcapsules were produced by the method described in example 2, with the exceptions that a mesh size of 18 to 30 and varying phase ratios of ethylcellulose:pellets were used.

| Time (hours) | Sample 1 | Sample 2 % Released | Sample 3 |
| --- | --- | --- | --- |
| 1 | 4.2 | 7.0 | 10.2 |
| 4 | 37.6 | 47.2 | 59.3 |
| 8 | 61.4 | 71.8 | 78.8 |
| 12 | 74.0 | 83.0 | 90.8 |

Sample 1 - phase ratio of 5:1, ethylcellulose:pellets
Sample 2 - phase ratio of 7.5:1, ethylcellulose:pellets
Sample 3 - phase ratio of 10:1, ethylcellulose:pellets

Example 8

Release rate of verapamil formulation

Verapamil microcapsules, produced in the same manner, but with differing phase ratios of ethylcellulose to loaded pellets from those produced in example 1, were analyzed using USP paddle method (900 ml of 0.1N HCl, 37 degrees C., 50 rpm) and standard techniques known to the art.

| Time (hours) | Sample 1 | Sample 2 % Released |
| --- | --- | --- |
| 1 | 1.3 | 15.8 |
| 2 | 1.7 | 29.5 |
| 4 | 3.3 | 52.3 |
| 8 | 7.3 | 80.6 |
| 12 | 17.9 | 92.8 |
| 16 | 26.2 | 98.0 |
| 20 | 34.4 | 103.8 |
| 24 | 42.2 | |

Sample 1 - microencapsulated at a 5:1 phase ratio
Sample 2 - microencapsulated at a 10:1 phase ratio

Example 9

Comparison of prilled v. non-prilled granules

Irregularly shaped granules were loaded with verapamil using the method of example 1. Microcapsules were then prepared using the method of example 1 at a phase ratio of 10:1, ethylcellulose:pellets. One hundred percent release was realized in two hours using the USP paddle method in 900 ml of 0.1N HCl at 37 degrees C. and 50 rpm.

The above experiment was repeated with the additional step of prilling the pellets prior to microencapsulation. One hundred percent release was realized in 16 hours.

Example 10

Release rates of diltiazem microcapsules in varying pH

Diltiazem microcapsules, produced in the same manner as those produced in example 2, but with a phase ratio of 10:1 ethylcellulose:pellets, were analyzed using USP Paddle method (900 ml fluid, 37 degrees C., 75 rpm) and standard techniques known to the art.

| Time (hours) | Sample 1 | Sample 2 % Released | Sample 3 |
| --- | --- | --- | --- |
| 1 | 10.4 | 6.1 | 6.6 |
| 4 | 46.2 | 42.0 | 36.6 |
| 8 | 72.4 | 65.0 | 64.6 |
| 12 | 85.4 | 80.0 | 80.3 |

Sample 1 - water
Sample 2 - 1.2 pH buffer
Sample 3 - 6.8 pH buffer

Figure 1:
FIG. 1 depicts verapamil microcapsules at a magnification of 10×. These non-prilled microcapsules were prepared in the same manner as those of example 9 with a phase ratio of 10:1.
Figure 2:
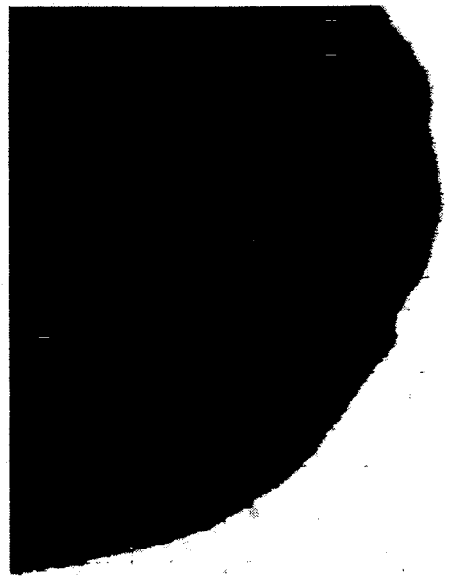
FIG. 2 depicts verapamil microcapsules at a magnification of 10×. These prilled microcapsules were prepared in the same manner as those of example 9 with a phase ratio of 10:1.
Figure 3:
FIG. 3 depicts diltiazem microcapsules at a magnification of 10×. These non-prilled microcapsules were prepared in the same manner as those of example 9 with a phase ratio of 10:1.
Figure 4:
FIG. 4 depicts diltiazem microcapsules at a magnification of 10×. These prilled microcapsules were prepared in the same manner as those of example 9 with a phase ratio of 10:1.

The above description is for the purpose of teaching the person of ordinary skill in the art how to practice the present invention and is not intended to detail all those obvious modifications and variations of it which will become apparent to the skilled worker upon reading the description or to limit the invention in any way. It is intended, however, that all such obvious modifications and variations be included within the scope of the present invention and by the following claims.

What is claimed is:

1. A process for the preparation of controlled release microencapsulated calcium channel blockers comprising:
   a) loading a calcium channel blocker from solution onto pellets;
   b) prilling the loaded pellets;
   c) screening the pellets to obtain those from about 12 to about 50 mesh;
   d) dispersing ethylcellulose in an organic solvent to form a dispersion;
   e) adding the loaded pellets of step (c) to the dispersion of step d to form a mixture in which the phase ratio of the ethylcellulose to the loaded pellets is from about 1:5 to about 1:50;
   f) heating the mixture with agitation until the ethylcellulose is in solution;
   g) cooling the solution to solidify the ethylcellulose and achieve microencapsulation;
   h) recovering the microcapsules from the solution;
   i) drying the microcapsules;
   j) screening the dried microcapsules to obtain dried microcapsules from about 10 to about 50 mesh.

2. The process of claim 1, wherein loading a calcium channel blocker from solution onto pellets comprises forming a mixture of the calcium channel blocker and a binder of water soluble polymer which is insoluble in the organic solvent of step (d); and applying the mixtures to the pellets.

3. The process of claim 2, wherein the binder is polyvinylpyrrolidone.

4. The process of claim 1, further comprising dispersing a phase separation-inducing polymer in the organic solvent of step (e) and heating the mixture of step (f) until the phase-separating polymer is in solution.

5. The process of claim 4, wherein the phase separation-inducing polymer of step (d) is polyethylene.

6. The process of claim 1, further comprising coating the screened pellets of step with a coating of a water insoluble binder which is insoluble in the organic solvent of step (d).

7. The process of claim 6, wherein the binder is polyvinylpyrrolidone.

8. The process of claim 1, wherein the pellets comprise a pharmaceutically acceptable, non-functional solid carrier.

9. The process of claim 1, wherein the pellets comprise crystals of the calcium channel blocker.

10. The process of claim 1, further comprising filling gelatin capsules with the microcapsules resulting from step (j).

11. The process of claim 1, wherein the calcium channel blocker is one of the group consisting of diltiazem, verapamil, and nifedipine.

12. The process of claim 1, wherein the organic solvent of step (d) is cyclohexane.

13. The process of claim 1, wherein the phase ration of the ethylcellulose to the loaded pellets is from about 1:20 to about 1:25.

14. The process according to claim 1, wherein the screened pellets of step (c) are between 12 and 30 mesh.

15. The process according to claim 1, wherein the screened pellets of step (c) are between 14 and 20 mesh.

16. A controlled release formulation made according to the process of claim 9.

17. A controlled release formulation made according to the process of claim 10.

18. The formulation of claim 17, wherein the release rate is approximately zero order.

* * * * *